United States Patent
Coszach et al.

(10) Patent No.: US 9,573,925 B2
(45) Date of Patent: Feb. 21, 2017

(54) PROCESS FOR RECOVERING AND IMPROVING PRODUCTION OF MESO-LACTIDE FROM A CRUDE LACTIDE CONTAINING STREAM

(71) Applicant: FUTERRO S.A., Escanaffles (BE)

(72) Inventors: Philippe Coszach, Escanaffles (BE); Denis Mignon, Braine-l'Alleud (BE)

(73) Assignee: FUTERRO S.A., Escanaffles (BE)

(*) Notice: Subject to any disclaimer, the term of this patent is extended or adjusted under 35 U.S.C. 154(b) by 0 days.

(21) Appl. No.: 14/787,117

(22) PCT Filed: May 6, 2014

(86) PCT No.: PCT/EP2014/059220
§ 371 (c)(1),
(2) Date: Oct. 26, 2015

(87) PCT Pub. No.: WO2014/180836
PCT Pub. Date: Nov. 13, 2014

(65) Prior Publication Data
US 2016/0068505 A1    Mar. 10, 2016

(30) Foreign Application Priority Data

May 6, 2013   (EP) .................................... 13166707

(51) Int. Cl.
*C07D 319/12*    (2006.01)
*B01D 3/14*    (2006.01)
*B01D 9/00*    (2006.01)

(52) U.S. Cl.
CPC ............ *C07D 319/12* (2013.01); *B01D 3/143* (2013.01); *B01D 9/004* (2013.01); *B01D 2009/0086* (2013.01)

(58) Field of Classification Search
CPC ..................................................... C07D 319/12
USPC .......................................................... 549/274
See application file for complete search history.

(56) References Cited

U.S. PATENT DOCUMENTS

| | | | |
|---|---|---|---|
| 5,214,159 A | 5/1993 | Muller et al. | |
| 5,357,034 A | 10/1994 | Fridman et al. | |
| 5,521,278 A | 5/1996 | O'Brien et al. | |
| 6,313,319 B1* | 11/2001 | Ohara ................... | A23C 11/06 426/133 |
| 2011/0190512 A1 | 8/2011 | Mariage et al. | |

OTHER PUBLICATIONS

International Search Report issued in PCT/EP2014/059220, dated May 28, 2014, 3 pages.

* cited by examiner

*Primary Examiner* — Taofiq A Solola
(74) *Attorney, Agent, or Firm* — Adolph Locklar

(57) ABSTRACT

A process for the recovery and production of meso-lactide from a crude lactide containing stream may include subjecting a starting crude lactide stream to a first distillation step to obtain: a top stream mainly containing meso-lactide; a bottom stream; and a side stream mainly containing L-lactide and meso-lactide. The process may include recovering the side stream and subjecting the side stream to a melt crystallization step to obtain: a first purified stream mainly containing L-lactide; and a drain stream mainly containing meso-lactide and L-lactide. The process may include recovering the top stream and drain stream, and subjecting the top stream and drain stream to a second distillation step to obtain a second purified stream containing L-lactide and meso-lactide.

17 Claims, 3 Drawing Sheets

Figure 1:
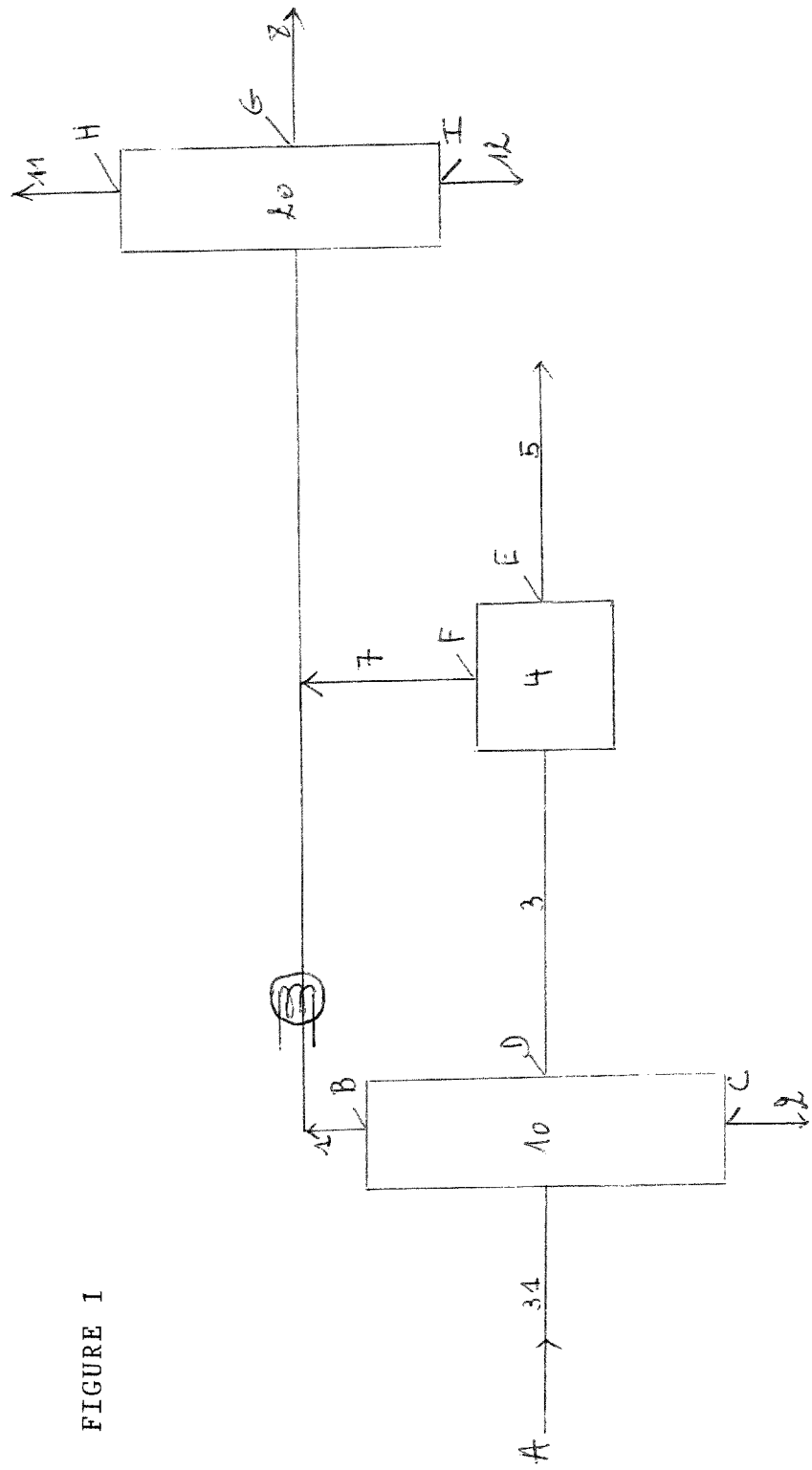

PROCESS FOR RECOVERING AND IMPROVING PRODUCTION OF MESO-LACTIDE FROM A CRUDE LACTIDE CONTAINING STREAM

CROSS-REFERENCE TO RELATED APPLICATIONS

This application is a National Stage Entry of PCT/EP2014/059220, filed on May 6, 2014, which claims priority from EP 13166707.3, filed on May 6, 2013, the entireties of which are incorporated herein by reference.

FIELD OF INVENTION

The present invention relates to a process for the recovery of meso-lactide free from impurities and heavy compounds, from a crude lactide containing stream dedicated to be purified to produce L-lactide and/or D-Lactide.

The present invention also relates to the joint production of L-lactide and meso-lactide in high yield, and finally it further relates to an apparatus for such recovery of meso-lactide and L-lactide as used in the present process.

BACKGROUND OF THE INVENTION

As concern for the environment grow, biodegradable polymers are becoming of increasing commercial interest as a substitute for conventional and less degradable synthetic polymers such as polyolefins and polyurethanes. The use of biodegradable polymers in areas of packaging and textiles is therefore steadily growing. Consequently, much research is directed to the synthesis of these biodegradable materials. Among the various biodegradable polymers, polylactide (PLA) is one of the most commonly used and studied.

PLA is an aliphatic polyester based on lactic acid, the latter being obtained by fermentation of sugars and/or starch. PLA is therefore derived from renewable vegetables and is biodegradable by composting.

PLA is prepared from lactide by ring-opening polymerization. Lactide, which is a dimeric cyclic ester of lactic acid is in turn formed by dehydrating aqueous lactic acid to form a mixture of oligomers, which mixture is then depolymerized to form lactide. In order to prepare PLA of a high quality, it is very important to use lactide of a high purity. The lactide needs therefore to be purified to a high extent before ring-opening polymerization may take place to prepare PLA of a high quality.

A variety of lactide purification processes are known, that usually comprise one or more integrated distillation, condensation and melt crystallization steps, like in U.S. Pat. Nos. 5,521,278, 5,357,034, 5,214,159.

However, none of them suggest improving the production of meso-lactide while producing L-lactide in high yield from the crude lactide stream to be purified.

It is also well known that with the increasing demand in PLA polymers, it appears that a range of PLA polymers with various concentrations in enantiomers L- and D- is more and more interesting; but there is a need for easy means to obtain such type of polymers, and mainly to avoid the implementation of a second polymerization unit for D-Lactide or meso-lactide.

Presently, for the usual applications involving L-Lactide, it is requested to have such L-Lactide with a high optical purity; a usual process to get such a purity often needs a step to separate meso-lactide. One has to do with controlling the proportion of D-enantiomers in the lactide stream that is taken for the polymerization step.

It is also important to control the ratio of L- and D-enantiomers in the lactide stream. It is known that removing meso-lactide from the lactide stream has the effect of reducing the proportion of D-enantiomers, which leads to the production of a more crystalline grade of polylactide. In new applications it is more and more interesting to obtain copolymers having a low content of D-enantiomers, so broadening the range of grades of PLA which are needed to cover the different applications where PLA may be used; those grades of PLA may contain various amounts of D-enantiomers ranging from about 1% by weight to more than 10% by weight, depending of the final use desired.

In usual process to prepare PLA, mostly on the basis of the L-lactide enantiomer, these processes comprise a purification step of the crude lactide to selectively separate the L-lactide enantiomer from the crude lactide stream.

Concerning the meso-lactide, it is also separated from the crude lactide stream, but the separated stream will also comprise certain impurities such as water, lactic acid as well as dimers and trimers of lactic acid.

With the usual methods of separation, like distillation and/or melt crystallization, there occurs a concentration of the impurities in the meso-lactide stream. Although it is of common practice to blend impurities containing meso-lactide stream with the pure L-lactide stream in proportion not higher than about 15% by weight, this leads to production of less crystalline polylactide, and this is the reason why much or all the meso-lactide recovered in such processes, is simply discarded, and therefore, this drastically reduces the overall yield in lactide. Solutions have already been envisioned in the art, but they are not satisfactory.

It is therefore an object of the present invention to provide a process to recover a purified meso-lactide either alone or in the presence of L-lactide, from a crude lactide stream, said purified meso-lactide having a limited amount of acid impurities, the content of which is expressed in the form of mEq/kg and is not exceeding 50 mEq/kg, preferably less than 30 mEq/kg and most preferably less than 15 mEq/kg, in order to blend such meso-lactide with purified L-lactide stream to prepare suitable PLA polymers useful for the different applications where the presence of D-enantiomers are needed.

Another object of the invention is to provide such a process where the polymer obtained with the recovered meso-lactide does not present the drawbacks of the prior art.

It is a further object of the present invention to provide a process enabling to use recovered meso-lactide for blending with L-lactide.

It is still a further object of the present invention to increase the overall yield in lactides (polymerizable lactides/crude lactides fed) up to high values equal to or higher than 90% and most preferably higher than 95%. By lactides, it is meant the L-lactide, the D-lactide and the meso-lactide.

Finally it is an object of the present invention to provide an apparatus to operate the process of the invention.

At least one of the objects is fullfilled by the present invention.

Applicants have now found that meso-lactide from which certain impurities have been substantially removed like water, lactic acid, lactic acid oligomers, catalysts derivatives, light and heavy colour impurities as for instance sugars, nutrients, proteins and amino acids, is a source of D-enantiomers to prepare suitable PLA grades containing L- and D-enantiomers.

The process of the invention for the recovery and production of meso-lactide from a crude lactide containing stream comprises the steps of:
a. Subjecting a starting crude lactide stream (A) to a first distillation step to obtain:
   a top stream (B) mainly containing meso-lactide,
   a bottom stream (C) and
   a side stream (D) mainly containing L-lactide and meso-lactide;
b. Recovering the side stream (D) and subjecting said stream to a melt crystallization step to obtain:
   a first purified stream (E) mainly containing L-lactide and
   a drain stream (F) mainly containing meso-lactide and L-lactide;
c. Recovering top stream (B) and drain stream (F);
d. Subjecting top stream (B) and drain stream (F) to a second distillation step to obtain a second purified stream (G) containing L-lactide and meso-lactide.

LIST OF FIGURES

Figure 2:
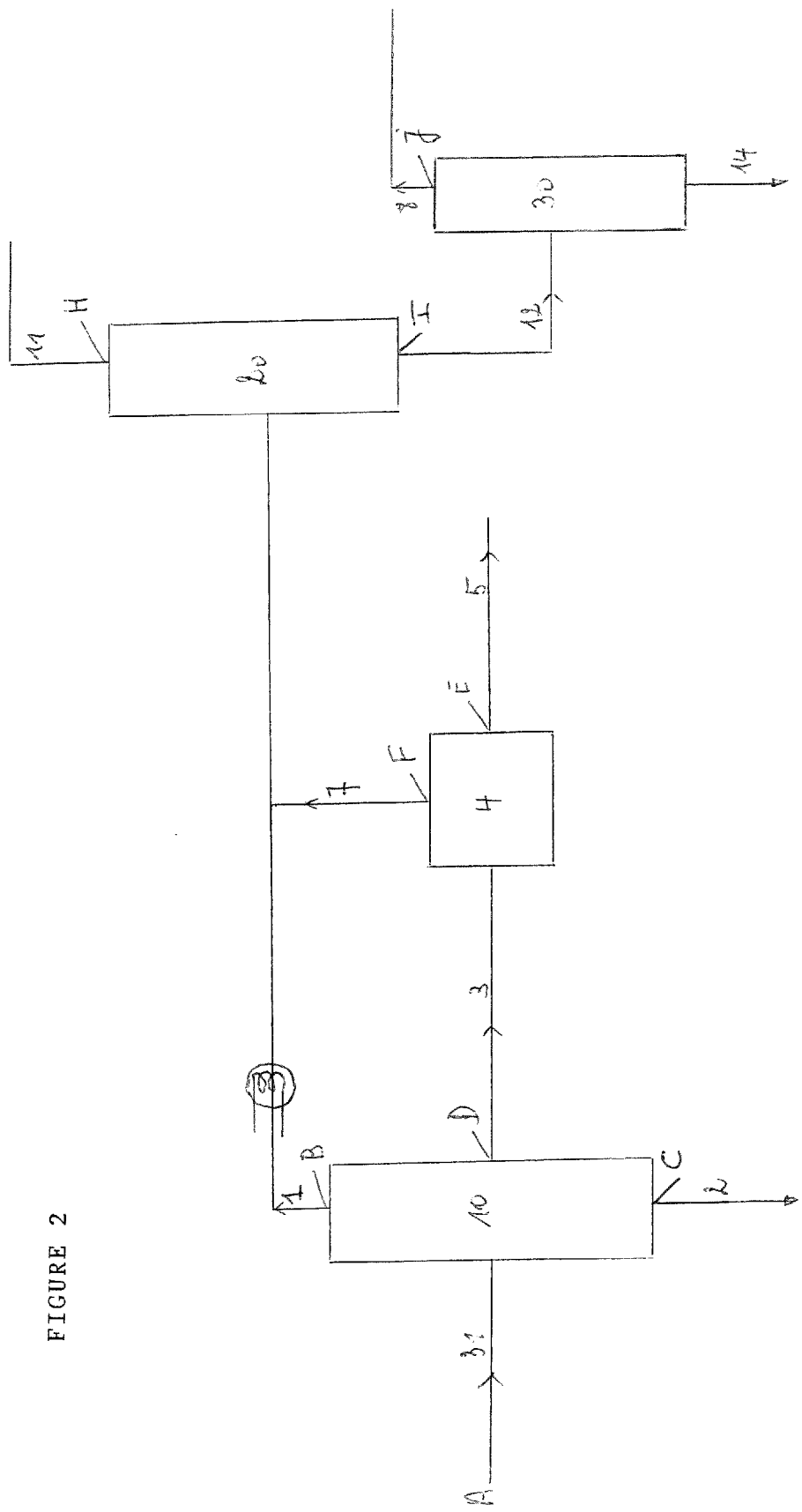
Figure 3:
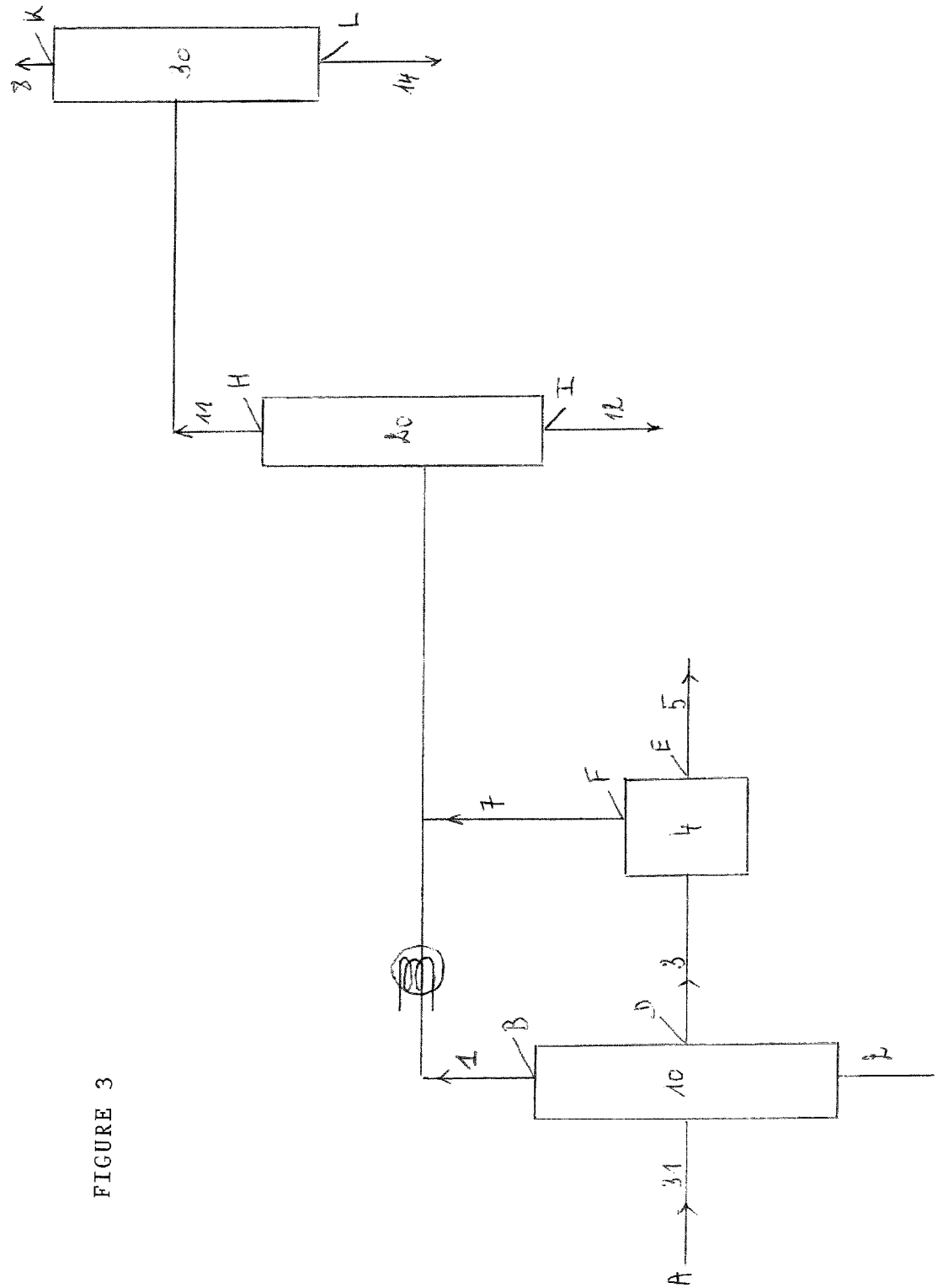

FIG. 1 shows the flow sheet of the process according to the invention with two distillation operation systems.
FIG. 2 shows the flow sheet of the process according to the invention with three distillation operation systems wherein the purified lactides are withdrawn at the top of the third distillation column.
FIG. 3 shows the flow sheet of the process according to the invention with three distillation operation systems wherein the purified lactides are withdrawn at the bottom of the third distillation column.

DETAILED DESCRIPTION OF THE INVENTION

The present invention provides a process for the recovery of meso-lactide from purification of a crude lactide-containing stream. In accordance with the present invention the source of lactide-containing stream may vary. In this respect it is observed that the lactide from which PLA can be prepared may be obtained by various routes. For instance, the stream may result from a lactide production, from a recycled lactide or PLA, or from the devolatilization of PLA. The lactide-containing stream to be purified can be prepared by a two steps polymerization/depolymerization process, in which first lactic acid from a feed source is polymerized to a relatively low molecular weight polylactic acid, which polylactic acid is then heated, generally in the presence of a catalyst, to depolymerize the low molecular weight polylactic acid to lactide. The lactide will usually be recovered as a component of a vapor product stream, which stream will also contain impurities such as water, lactic acid and oligomers of lactic acid. These impurities need to be removed from the vapor product stream because they are capable of participating in the ring opening reactions with lactide, so resulting in a lower quality and yield of lactide.

The crude lactide stream to be purified in accordance with the present process may comprise L-lactide, D-lactide, meso-lactide and mixtures thereof. Preferably the crude lactide stream contains mainly L-lactide.

According to the invention, the first step (a) of the recovery and production of meso-lactide, mainly under the form of a mixture meso-lactide and L-lactide, is carried out by passing the crude lactide stream (31) into a separation unit such as a distillation column (10). Preferably, the distillation column is a multi-stage distillation column. The distillation column can be any type of known distillation column such as a tray column or a packed column. Preferably the distillation column is a packed column. Generally, the distillation column has a number of theoretical stages (NTS) in the range from 6 to 30.

The first step (a) is suitably carried out at a temperature in the range of from 80-180° C., preferably in the range of from 100-160° C., and a pressure in the range of from 3-50 mbara, preferably in the range of from 7-20 mbara.

The more volatile components of the lactide-containing stream (A) to be purified, forming stream (B), will be more easily evaporated through the top of the distillation column (10) than less volatile components such as L-lactide, oligomers of lactic acid and heavy impurities, which will be recovered through the bottom and the side draw of the distillation column. Hence, the more volatile components generally identified as water, lactic acid, catalyst derivatives and gaseous lactide, like meso-lactide, will move to the upper part of the column and will be evacuated through pipe (1). It is also known that the yield of the distillation column has an impact on the type of the most volatile components evacuated through pipe (1); for instance a lower yield of the column, typically below 90%, will increase the fraction of L-lactide; on the contrary, if the yield of the column is higher than 95% the fraction of lactide present is considerably reduced and it might not be necessary to send said top stream (B) substantially free of lactide to a second distillation system. Generally the top stream of the most volatile components (B) flowing through pipe (1) is thereafter sent to a further distillation system which may comprise one or more distillation columns. The upper part of the first distillation column (10) is preferably connected to a condensation unit in which the various volatile components are condensed and contains mainly water, meso-lactide, L-lactide and lactic acid.

The lactide-containing liquid fraction and the less volatile components, both obtained in first step (a), are treated in the lower part of distillation column (10) and withdrawn through the side draw or the bottom forming respectively streams (D) and (C).

After evacuation of top stream (B) of column (10) through pipe (1) with the more volatile components, and the withdrawal of the less volatile components through bottom stream (C) through pipe (2), which is either hydrolyzed and sent back to the Lactic Acid Unit, or suitably recycled to the oligomerization step of the overall process, then, the important lactide-containing fraction of step (a) is suitably withdrawn from the distillation column (10) via a side draw, and constituting side stream (D) flowing through pipe (3) which is sent to a unit where the melt-crystallization (4) is carried out.

Suitably, said lactide containing fraction withdrawn through the side draw by pipe (3) may contain in the range of from 90-99.5 wt %, preferably in the range of from 95-99 wt % of L-lactide and in the range of from 0-10 wt %, preferably in the range of from 0-5 wt % meso-lactide, based on the total mass flow rate of the lactide containing fraction of the side draw. Suitably the lactide containing fraction of the side draw has a ratio of L-lactide to meso-lactide in the range of from 1 to 100, preferably in the range of from 10 to 50.

In the event the lactide containing fraction withdrawn by the side draw through (3) is not in the liquid phase, but rather in the vapor phase, a condensation unit may be implemented to treat the vapor phase lactide containing fraction.

At least part of the lactide containing stream (D) of pipe (3) as obtained in step (a) is subjected to a melt crystallization (4) to recover a purified lactide containing stream (E) through pipe (5), mainly containing L-lactide, and a drain stream (F) containing L-lactide and meso-lactide, in pipe (7).

The melt crystallization (4) is suitably carried out continuously in a melt crystallization unit having a cold surface, and is suitably carried out in one or more crystallization units in series. Any type of melt crystallization unit without need of a solvent can be used in accordance with the present invention while the crystallization process may be conducted either in continuous mode or batch mode or still under a pseudo-continuous mode of operation. Suitable examples of melt crystallization units that can be used in the apparatus of the invention include static, falling film and suspension melt crystallization unit. The skilled person will also understand that various combinations of the different types of melt crystallization sub-units may be used in the apparatus of the present invention, as well as different types of melt crystallization stages.

Suitably the melt crystallization (4) is carried out at a temperature which remains in the range of the crystallization freezing temperature and a temperature ranging well below the boiling point of lactide.

Suitably, the meso lactide content in stream flowing in pipe (5) is in the range of from 0-1 wt %, preferably in the range of from 0-0.5 wt %.

Suitably, in the crystallization unit (4) the volume of liquid is drained outside through pipe (7) forming drain stream (F) which is mainly containing meso-lactide and L-lactide.

According to steps (b) and (c) of the process of the present invention, top stream (B) flowing through pipe (1) coming from distillation column (10) is recovered and contains mainly meso-lactide, while drain stream (F) flowing in pipe (7) is also recovered and contains mainly L-lactide and meso-lactide. According to the process of the present invention, it has been found that there is an interest to convey or combine as the case may be, both fractions which are rich in L-lactide and meso-lactide but are containing a limited amount of impurities which are heavy and viscous components.

According to the process of the present invention both streams (B) and (F) are conveyed or combined and subjected to a distillation operation in one or more distillation operation system. Preferably, said system comprises a distillation column (20) which is a multi-stage distillation column. The distillation column can be any type of known distillation column such as a tray column or a packed column. Preferably the distillation column is a packed column.

In the event of use of only one distillation column in this distillation operation system, said sole distillation column (20) is suitably operated at a temperature in the range of from 100 to 185° C., and a pressure in the range of from 3-50 mbara. Generally this distillation column (20) has from 20 to 50 theoretical stages.

According to an embodiment of the process of the present invention with one distillation column (20), the more volatile components which comprise mainly water and lactic acid are evaporated through pipe (11) for further treatments, while a mixture of purified L-lactide and meso-lactide having a D-enantiomer content of from 10 to 50 wt % is recovered through pipe (8), and whereas the less volatile components will move to the lower part of the column and will be withdrawn through pipe (12) for further treatment, which includes among others recycling or simple purge.

In a preferred embodiment of the present invention, two streams are recovered from column (20), a first stream (H) with the more volatile components like lactic acid and water are evaporated through pipe (11) and a second stream (I) with the less volatile components withdrawn through pipe (12) which are sent to a third distillation column (30) where a top stream (J) is recovered through pipe (8), and which comprises a mixture of purified L-lactide and meso-lactide having a D-enantiomer content of from 10 to 50 wt % preferably of from 20 to 40 wt % and a bottom stream which is withdrawn through pipe (14) for further treatment including among others recycling or simple purge.

In accordance with the process of the present invention, the purified stream (J) of pipe (8) is recovered and contains L-lactide and meso-lactide of high purity. The recovered purified lactide-containing stream contains 95 to 99.9 wt % lactide and more preferably 98 to 99.9 wt % lactide. Suitably, the purified lactide containing stream (J) to be recovered has a water content in the range of from 0 to 100 ppm and more preferably from 0 to 50 ppm, based on the total mass flow rate of the purified lactide containing stream. Suitably, the purified lactide containing stream has a residual acidity comprised between 0.1 to 30 mEq/kg and preferably between 0.5 and 15 mEq/kg and most preferably between 0.5 and 10 mEq/kg.

Such stream (J) of pipe (8) may be successfully blended with other L-lactide purified fraction in various proportions to cover the desired range of PLA polymer grade.

According to the process of the present invention the overall yield in lactides unexpectedly may be equal to or higher than 90% and even higher than 95%, which is a considerable advantage over the other processes in the art.

The present invention also relates to an apparatus for the purification of a crude lactide-containing stream comprising:

A first separation unit (10) which comprises one or more inlets, one or more outlets, and one or more side draws for withdrawing one or more lactides-containing fractions from the separation unit, said separation unit may comprise condensation means where needed;

A melt crystallization unit (4) comprising one or more inlets and one or more outlets;

A second separation unit (20) comprising one or more inlets for collecting the top stream of separation unit (10) and drain stream of melt crystallization (4), and one or more outlets;

Optionally a third separation unit (30) comprising one or more inlets for collecting the bottom fraction of separation unit (20) and one or more outlets to recover a stream of purified lactides.

According to one embodiment, the apparatus comprises:

A first separation unit (10) which comprises one or more inlets, one or more outlets, and one or more side draws for withdrawing one or more lactides-containing fractions from the separation unit;

A melt crystallization unit (4) comprising one or more inlets and one or more outlets;

A second separation unit (20) comprising one or more inlets for collecting the top stream (B) of separation unit (10) and drain stream (F) of melt crystallization (4), and one or more outlets for separating the light components including lactides on the one hand and the heavy components on the other hand;

A third separation unit (30) comprising one or more inlets for collecting the top fraction of separation unit (20) with light components and the lactides and one or more outlets to recover a stream of purified lactides (L).

According to another embodiment, the apparatus comprises:

A first separation unit (10) which comprises one or more inlets, one or more outlets, and one or more side draws for withdrawing one or more lactides-containing fractions from the separation unit;

A melt crystallization unit (4) comprising one or more inlets and one or more outlets;

A second separation unit (20) comprising one or more inlets for collecting the top stream (B) of separation unit (10) and drain stream (F) of melt crystallization (4), and one or more outlets for withdrawing the light components on the one hand and the heavy components including lactides on the other hand;

A third separation unit (30) comprising one or more inlets for collecting the bottom fraction of separation unit (20) with heavy components and the lactides and one or more outlets to recover a stream of purified lactides (J).

The separation units (10), (20) and (30) can suitably be any distillation column as described hereinbefore. Preferably, the separation units are multistage distillation columns. Usually, the distillation columns are packed distillation columns, the packing of which is preferably a commercially available packing such as for example ROMBOPACK S6M, BS-500MN, A3-500.

One embodiment of the present invention is illustrated in FIG. 1.

In FIG. 1, a crude-lactide containing stream (A) is led via pipe 31 to a distillation column (10). In distillation column (10) the crude lactide containing stream (A) is subjected to a multi-step fractionation process, thereby obtaining more volatile components such as water, lactic acid, meso-lactide and less volatile components such as liquid lactide and oligomers of lactic acid. The more volatile components are withdrawn from column (10) via pipe (1) and are forming top stream (B) mainly containing water, lactic acid, meso-lactide, whereas the less volatile components will move to the lower part of distillation column (10) and are withdrawn through pipe (2). A lactide containing fraction comprising volatile components is then withdrawn through side draw via pipe (3) and introduced, under the liquid phase, into melt crystallization unit (4). In the melt crystallization unit (4) a purified L-lactide containing stream (E) is recovered through pipe (5), and a drain stream (F), mainly containing meso-lactide and L-lactide, is withdrawn through pipe (7).

The drain stream (F) flowing through pipe (7) and top stream (B) of column (10) flowing through pipe (1) are conveyed, or combined if so desired, and sent to distillation column (20), thereby obtaining a top stream (H) with the more volatile components withdrawn through pipe (11), a stream (I) with the less volatile components withdrawn through pipe (12) and the recovery through pipe (8) of a stream (G) containing purified L-lactide, D-lactide and meso-lactide free from impurities, which is an advantage for the efficiency of the polymerisation of the lactide.

A preferred embodiment of the present invention is illustrated in FIG. 2 where the lactide containing streams (B) and (F) are supplied through pipes (1) and (7) to separation unit (20) where said both lactide containing streams (B) and (F) are subjected to a distillation operation in preferably a packed column comprising from 10 to 40, preferably 15 to 30 theoretical stages and operated at temperature comprised between 120-175° C., preferably between 145-165° C. and at a pressure of 10 to 40 mbara, thereby obtaining a top stream (H) with the more volatile components definitely withdrawn through pipe (11) and a stream (I) with the less volatile components, including all lactide species, withdrawn through pipe (12) supplied to a third distillation column (30), preferably a packed column comprising from 6 to 20 theoretical stages and operated at a temperature of from 120 to 185° C., preferably from 145 to 175° C. and at a pressure of from 5 to 20 mbara, from which a purified lactide stream (J), containing L-lactide, D-lactide and meso-lactide and a limited amount of other impurities not exceeding 50 mEq/kg, is recovered through pipe (8), while the less volatile components are definitely withdrawn through pipe (14) for further treatment like recycling or simply a purge.

The withdrawal of the purified lactide stream (J) through pipe (8) may be located at any suitable place in the neighbourhood of the top of column (30) or even as a side draw at a point located between the top of the distillation column and the top of the packing of said distillation column (30) in order to maximize the recovery of lactides. According to one embodiment, the purified lactide stream (J) may be withdrawn as a side-draw from the distillation column at a point located between the top of the distillation column and the bottom of the upper packing bed of said distillation column. According to another embodiment, the purified lactide stream (J) may be withdrawn as a side-draw from the distillation column at a point located between the bottom of the upper packing bed and the top of the middle packing bed of said distillation column.

In the instance that the purified lactide stream (J) through pipe (8) is not located at the top of the column, but rather as located as a side-draw in the neighbourhood of the top of column (30), a gaseous purge stream may be withdrawn from the top of column (30) in order to improve the purity of the purified lactide stream (J) through pipe (8).

According to another embodiment of the process of the present invention, as represented by FIG. 3, it is possible to modify the separation or distillation unit (20) and its operating conditions so as to have a distillation column (20), preferably a packed column comprising from 6 to 20 theoretical stages and operated at a temperature of from 120 to 185° C., preferably of from 145 to 175° C. and at a pressure of 5 to 20 mbara, so as to recover a top stream (H) flowing through pipe (11) and containing the more volatile components and all lactide species, while definitely withdrawing the heavies through the bottom stream (I) in pipe (12) for further treatment; the top stream (H) of column (20) is then supplied through pipe (11) to distillation column (30), preferably a packed column comprising from 10 to 40, preferably 15 to 30 theoretical stages and operated at a temperature comprised between 120 and 175° C., preferably between 140 and 165° C. and at a pressure of 10 to 40 mbara, from which a purified lactide stream (L), containing L-lactide, D-lactide and meso-lactide and a limited amount of other impurities, not exceeding 50 mEq/kg, is recovered from bottom stream through pipe (14), while the light components like lactic acid and water (K) are definitely withdrawn through top stream flowing through pipe (8).

Both distillation columns (20) and (30) when coupled in whatever embodiment of the process of the invention have a number of theoretical stages generally comprised in the range of 5 to 40. Particularly the distillation columns are packed columns; however the column dedicated to the definitive removal of the most volatile components, like lactic acid and water comprises preferably from 10 to 40 theoretical stages, more preferably from 15 to 30 theoretical stages and is operated at a temperature of from 120 to 175° C. and at a pressure of from 10 to 40 mbara while the column dedicated to the definitive withdrawal of the heavy components comprises preferably from 6 to 20 theoretical stages and is operated at a temperature of from 120 to 185° C. and at a pressure of from 5 to 20 mbara.

One of the advantages of the present invention is to recover a stream of purified L-lactide and meso-lactide containing a limited amount of impurities, not exceeding 50 mEq/kg, preferably lower than 30 mEq/kg and more preferably lower than 20 mEq/kg, which leads to a more efficient polymerization of the lactide.

The purified L-lactide and meso-lactide recovered by the process of the invention has a water content lower than 100 ppm, preferably lower than 50 ppm, and a residual acidity comprised between 0.1 and 30 mEq/kg, preferably comprised between 0.5 and 10 mEq/kg.

In achieving whatever of these preferred embodiments of the process of the present invention, the operating conditions of the distillation column dedicated to the definitive removal of the most volatile components, and more particularly the inlet temperature of the lactide stream, may be adjusted without departing of the process of the present invention, in view of optimizing the distillation column to balance between energy supply needed and the minimization of the degradation of the products to be recovered.

It is also well understood that the process of the present invention may also be applied to process for preparing PLA on the basis of the D-lactide enantiomer. The invention is further illustrated by means of the following non-limiting examples.

EXAMPLES

Analysis Methods

In the example, the lactic acid, the mesolactide, the L-lactide, the impurities, the L2A and oligomer (>2A) contents were determined by gas chromatography. The sample was prepared in acetonitrile and a silylation step was necessary before injection. The water content was determined by the Karl Fischer titration method.

The residual acidity was determined by colorimetric titration using sodium methoxide as titrant, phenol red as indicator and acetone as solvent.

A crude lactide stream, the composition of which is given in TABLE 1, is injected into distillation column (10) which is equipped with a reflux system on top of the column and a reboiler at the bottom of the column. The distillation column is packed with 2.7 meters of a structured packing ROMBOPACK S6M which is a metal sheets packing that yields 3.5 theoretical stages per meter. The crude lactide stream is subjected to distillation conditions, according to which a distillate is recovered through pipe (1) and then condensed, while a bottom product was withdrawn through pipe (2), and recycled to the Lactic Acid Unit.

The operating conditions of column (10) are as follows:
T° Feed: 114° C.
T° Top: 111° C.
T° Side draw: 132° C.
T° bottom: 172° C.
Top pressure: 9 mbara A gaseous lactide stream withdrawn as a side-draw through pipe (3) and then condensed before being supplied to the melt crystallization unit (4) from which a purified L-lactide stream flowing through pipe (5) is recovered, while the drain stream of the melt crystallization (4) is sent through pipe (7) and is combined with stream of pipe (1), the composition of the combined stream being given in TABLE 1 hereafter, before being supplied to a distillation column (20) which is packed with a structured packing BS-500MN that yields 30 theoretical stages and under the following operating conditions:

T° feed: 138° C.°
T° Top: 123° C.
T° bottom: 152° C.
Top pressure: 20 mbara and from which it is recovered a top stream with the more volatile components in pipe (11) comprising lactic acid and water, and a stream comprising the less volatile components is withdrawn through pipe (12), and sent to a further distillation column (30) which is packed with a structured packing A3-500 that yields 13 theoretical stages, and under the following operating conditions:

T° Feed: 151° C.
T° Top: 119° C.
T° Bottom: 155° C.
Top pressure: 10 mbara and from which it is recovered, through pipe (8), a stream of purified L-lactide and meso-lactide, whose D-enantiomer content is of 35.2%.

TABLE 1

|  | Feed 31 | Side Stream 3 | L-lactide 5 | Feed 1 + 7 | Meso-lactide L-lactide 8 |
|---|---|---|---|---|---|
| Lactic acid % | 0.83 | 0.11 | 0.01 | 12.77 | 0.07 |
| Meso-lactide % | 2.53 | 2.02 | 0.1 | 51.86 | 70.40 |
| L-lactide % | 89.94 | 97.46 | 99.89 | 23.18 | 29.49 |
| Cata deriva. % | 0.37 | 0 | 0 | 2.54 | 0.00 |
| L2A % | 1.84 | 0.36 | 0 | 7.4 | 0.04 |
| Oligo(>2A) % | 4.49 | 0.05 | 0 | 2.25 | 0.00 |
| Res Acidity mEq/kg | 370- | 35 | 1.36 | — | 10 |
| Water ppm | 390- | 210 | 15 | — | 25 |
| Flow Rate kg/h | 25 | 21.9 | 20.7 | 2.0 | 1.4 |
| Yield Global Lactides % | — | — | 89.72 | — | 95.80 |

The invention claimed is:

1. A process for the recovery and production of meso-lactide from a crude lactide containing stream, the process comprising:
    subjecting a starting crude lactide stream (A) to a first distillation step under distillation conditions comprising a temperature ranging from 80 to 180° C., a pressure ranging from 3 to 50 mbara and a number of theoretical stages of distillation (NTS) between 6 and 30 to obtain:
        a top stream (B) containing meso-lactide;
        a bottom stream (C); and
        a side stream (D) containing L-lactide and meso-latide;
    recovering the side stream (D) and subjecting the side stream (D) to a melt crystallization step to obtain:
        a first purified stream (E) containing L-lactide; and
        a drain stream (F) containing meso-lactide and L-lactide;
    recovering the top stream (B) and the drain stream (F); and
    subjecting the top stream (B) and the drain stream (F) to a second distillation step in a distillation column (20) operated at a temperature ranging from 100 to 185° C., a pressure ranging from 3 to 50 mbara and containing from 20 to 50 NTS to obtain a second purified stream (G) containing L-lactide and meso-lactide.

2. The process according to claim 1, wherein the side stream (D) is subjected to a melt crystallization step operated in the range of the lactide freezing temperature and below the temperature of the boiling point of lactide.

3. The process according to claim 1, wherein the second purified stream (G) containing L-lactide and meso-lactide has a D-enantiomer content between 10 and 50%.

4. The process according to claim 1, wherein the second distillation step is carried out in one or more than one distillation columns.

5. The process according to claim 1, wherein the second distillation step is carried out so that two streams are recovered comprising:
a top stream with residual lactic acid and water (H); and
a bottom stream (I) containing all lactide species;
wherein the bottom stream (I) is sent to a third distillation step where a top stream (J) is recovered and comprises a mixture of purified L-lactide and meso-lactide having a D-enantiomer content ranging between 10 and 50%.

6. The process according to claim 5, wherein the third distillation step is carried out in a distillation column, wherein the top stream (J) is withdrawn as a side-draw from the distillation column at a point located between a top of the distillation column and a top of packing of the distillation column.

7. The process according to claim 1, wherein the second distillation step is carried out so that two streams are recovered comprising a bottom stream with heavy components, which is withdrawn, and a top stream (H) with residual lactic acid, water and all lactide species, which is then sent to a third distillation step wherein a top stream (K) is recovered comprising lactic acid and water, and a bottom stream (L) is recovered comprising a mixture of a purified L-lactide and meso-lactide with a D-enantiomer content ranging between 10 and 50%.

8. The process according to claim 1, wherein a distillation column dedicated to the definitive removal of most volatile components, including lactic acid and water, comprises a number of theoretical stages ranging between 10 and 40 and is operated at a temperature of from 120 to 175° C. and at a pressure of from 10 to 40 mbara.

9. The process according to claim 1, wherein a distillation column dedicated to the definitive withdrawal of heavy components comprises a number of theoretical stages comprised between 6 and 20 and is operated at a temperature comprised between 120 to 185° C. and at a pressure between 5 and 20 mbara.

10. The process according to claim 1, wherein the starting crude lactide stream (A) is subjected to the first distillation step in a packed column having from 6 to 30 theoretical stages and is operated at a temperature of from 80-180° C. and a pressure of from 3 to 50 mbara, from which are recovered the top stream (B), the side stream (D) which is further subjected to the melt crystallization to recover L-lactide, and the bottom stream (C) which is withdrawn;
wherein the top stream (B) containing meso-lactide and the drain stream (F) of the melt crystallization are subjected to the second distillation step in a first packed distillation column having from 10 to 40 theoretical stages and is operated at a temperature of from 120 to 175° C. and a pressure of from 10 to 40 mbara, to recover a top stream (H) comprising lactic acid and water, and a bottom stream (I) that is sent to a second packed distillation column of the second distillation step; and
wherein the second packed distillation column comprises from 6 to 20 theoretical stages and is operated at a temperature of from 120 to 185° C. and a pressure of from 5 to 20 mbara to recover a top stream (J) of purified meso-lactide and L-lactide at a top of the second packed distillation column and a bottom stream containing heavy components and oligomer of lactide that is withdrawn.

11. Purified L-lactide and meso-lactide recovered by the process of claim 1, wherein a water content of the purified L-lactide and meso-lactide is lower than 100 ppm and a residual acidity of the purified L-lactide and meso-lactide is between 0.1 and 30 mEq/kg.

12. An apparatus for the purification of a crude lactide containing stream comprising:
a first separation unit comprising one or more inlets, one or more outlets, and one or more side draws for withdrawing one or more lactide-containing fractions from the first separation unit;
a melt crystallization unit comprising one or more inlets and one or more outlets; and
a second separation unit comprising one or more inlets for collecting a top stream of the first separation unit and a drain stream of the melt crystallization unit, and one or more outlets.

13. The apparatus according to claim 12, further comprising a third separation unit comprising one or more inlets for collecting a lactide fraction of the second separation unit, and one or more outlets to recover a stream of purified lactides.

14. The apparatus according to claim 12, wherein the second separation unit separates light components including lactides and heavy components, and wherein the apparatus further comprises a third separation unit comprising one or more inlets for collecting a top fraction of the second separation unit with light components including lactides and one or more outlets to recover a stream of purified lactides (L).

15. The apparatus according to claim 12, wherein the second separation unit comprises one or more inlets for collecting a top stream (B) of the first separation unit and a drain stream (F) of the melt crystallization unit, and one or more outlets for withdrawing light components and heavy components including lactides, and wherein the apparatus further comprises a third separation unit comprising one or more inlets for collecting a bottom fraction of the second separation unit with heavy components and lactides and one or more outlets to recover a stream of purified lactides.

16. The process of claim 1, wherein the distillation conditions for the first distillation step comprise a temperature range of 100 to 160° C.

17. The process of claim 1, wherein the distillation conditions for the first distillation step comprise a pressure ranging from 7 to 20 mbara.

* * * * *